United States Patent
Bernier et al.

(10) Patent No.: US 10,045,785 B2
(45) Date of Patent: Aug. 14, 2018

(54) INFERIOR VENA CAVA (IVC) SHUNT, DOUBLE-BALLOON CATHETER FOR OCCLUSION AS A SURGICAL TOOL

(71) Applicant: THE JOHNS HOPKINS UNIVERSITY, Baltimore, MD (US)

(72) Inventors: Wes Bernier, Baltimore, MD (US); Calvin Chang, Baltimore, MD (US); James H. Black, Baltimore, MD (US); David T. Efron, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 459 days.

(21) Appl. No.: 14/889,326

(22) PCT Filed: May 6, 2014

(86) PCT No.: PCT/US2014/036970
§ 371 (c)(1),
(2) Date: Nov. 5, 2015

(87) PCT Pub. No.: WO2014/182699
PCT Pub. Date: Nov. 13, 2014

(65) Prior Publication Data
US 2016/0081692 A1  Mar. 24, 2016

Related U.S. Application Data

(60) Provisional application No. 61/819,987, filed on May 6, 2013.

(51) Int. Cl.
*A61B 17/12* (2006.01)
*A61M 25/10* (2013.01)
*A61M 27/00* (2006.01)

(52) U.S. Cl.
CPC .. *A61B 17/12045* (2013.01); *A61B 17/12136* (2013.01); *A61M 25/1011* (2013.01);
(Continued)

(58) Field of Classification Search
CPC .. A61M 2025/1015; A61M 2025/1095; A61M 2025/1052; A61M 27/002; A61M 25/1011; A61B 17/12045
See application file for complete search history.

(56) References Cited

U.S. PATENT DOCUMENTS

| | | |
|---|---|---|
| 5,674,198 A | 10/1997 | Leone |
| 5,893,841 A | 4/1999 | Glickman |
| 6,148,825 A | 11/2000 | Anderson et al. |

FOREIGN PATENT DOCUMENTS

| | | |
|---|---|---|
| WO | 95-05209 A1 | 2/1995 |
| WO | 99-29227 A2 | 6/1999 |

OTHER PUBLICATIONS

International Search Report and Written Opinion dated Sep. 12, 2014, from related PCT Patent Application No. PCT/US2014/036970.

*Primary Examiner* — Leslie Deak
(74) *Attorney, Agent, or Firm* — Casimir Jones, S.C.; Jeffrey W. Childers (57) ABSTRACT

A double-balloon inferior vena cava (IVC) shunt for use in controlling blood loss and simultaneously maintaining venous return is disclosed. The IVC shunt comprises a first balloon-catheter unit and second balloon-catheter unit that are slidably coupled to one another to form an adjustable shunt. The first and second balloons in the shunt are independently inflatable. The double-balloon shunt is readily adjustable to fit the dimensions of the injured region.

6 Claims, 13 Drawing Sheets

(52) U.S. Cl.
CPC ... *A61M 27/002* (2013.01); *A61M 2025/1015* (2013.01); *A61M 2025/1052* (2013.01); *A61M 2025/1095* (2013.01)

INFERIOR VENA CAVA (IVC) SHUNT, DOUBLE-BALLOON CATHETER FOR OCCLUSION AS A SURGICAL TOOL

CROSS-REFERENCE TO RELATED APPLICATIONS

This application is a 35 U.S.C. § 371 National Stage Entry of International Application No. PCT/US2014/36970 having an international filing date of May 6, 2014, which claims the benefit of U.S. Provisional Patent Application No. 61/819,987, filed May 6, 2013, the contents of which are herein incorporated by reference in their entirety.

BACKGROUND

The inferior vena cava (IVC) is often injured in trauma to the abdominal area. The IVC is the large vein that carries de-oxygenated blood from the lower half of the body into the right atrium of the heart. Medical procedures typically used to repair traumatic IVC injuries often utilize shunts to control blood loss prior to repair of the injured site. In one example, double-balloon shunts are used to occlude blood flow on both sides (proximal and distal) of an IVC injury site. One of the limitations of IVC shunts known in the art for use in IVC repair is that they typically are fixed balloon shunts that may not adequately occlude blood flow and maintain sufficient venous return during repair of an IVC injury.

SUMMARY

In some aspects, the presently disclosed subject matter provides an inferior vena cava shunt comprising: a first catheter and a second catheter, wherein the first catheter and the second catheter are formed from two concentric hollow shafts that can be slidably coupled to one another to form an adjustable shunt region; wherein the first catheter comprises a first hollow shaft and a first inflatable balloon, wherein the first inflatable balloon is sealed around an outside surface of the first hollow shaft, and wherein the first hollow shaft is open at a leading end and open at an opposite trailing end, and wherein the first hollow shaft passes through the first inflatable balloon; wherein the first catheter further comprises a lumen formed in a wall of the first hollow shaft, wherein the lumen comprises one or more channels configured to provide a fluid path for inflating and/or deflating the first inflatable balloon, wherein the lumen comprises one or more inlets at an end of the lumen proximate to the trailing end of the first hollow shaft and one or more outlets at an opposite end of the lumen, and wherein the one or more outlets is located within a cavity of the first inflatable balloon; wherein the first hollow shaft further comprises a plurality of openings configured to provide a fluid path for venous blood into the first hollow shaft; and wherein the second catheter comprises a second hollow shaft and a second inflatable balloon, wherein the second inflatable balloon is sealed around an outside surface of the second hollow shaft, and wherein the second hollow shaft is tapered and closed at a leading end and open at an opposite trailing end, and wherein the second hollow shaft passes through the second inflatable balloon; wherein an outside diameter of the second hollow shaft is smaller than an inside diameter of the first hollow shaft such that the second hollow shaft can be slidably fitted into the first hollow shaft; wherein the second catheter further comprises a lumen formed in a wall of the second hollow shaft, wherein the lumen comprises one or more channels configured to provide a fluid path for inflating and/or deflating the second inflatable balloon, wherein the lumen comprises one or more inlets at an end of the lumen proximate to the trailing end of the second hollow shaft and one or more outlets at an opposite end of the lumen, and wherein the one or more outlets is located within a cavity of the second inflatable balloon; wherein the second hollow shaft further comprises a plurality of slits running longitudinally along the length of the second hollow shaft from the trailing end of the second hollow shaft to the opposite end thereof; and wherein the second hollow shaft further comprises a plurality of openings configured to provide a fluid path for venous blood out of the second hollow shaft; and wherein the first inflatable balloon and the second inflatable balloon can be inflated or deflated independently.

In other aspects, the presently disclosed subject matter provides a method for occluding an injured area of an inferior vena cava while maintaining venous return thereto, the method comprising: providing a presently disclosed inferior vena cava shunt; inserting the shunt into a femoral vein of a subject; guiding the shunt into the inferior vena cava to the injured area; adjusting a distance between the first inflatable balloon of the first catheter and the second balloon of the second catheter to fit one or more dimensions of the injured region, wherein the distance is adjusted by sliding the second catheter into or out of the first catheter; inflating the first inflatable balloon and the second inflatable balloon, wherein the inflated first balloon occludes a proximal side of the injured area and the inflated second balloon occludes the distal side of the injured area; and wherein the adjustable shunt region maintains blood flow to the injured area.

In yet other aspects, the presently disclosed subject matter provides a method for delivering a chemotherapeutic agent for treating a liver cancer, the method comprising: providing a presently disclosed shunt; forming one or more additional openings in the adjustable shunt region thereof, wherein the one or more additional openings are configured for delivering one or more chemotherapeutic agents to the liver; and implanting the shunt comprising one or more chemotherapeutic agents into the inferior vena cava for delivering the one or more chemotherapeutic agents to the liver.

In still yet other embodiments, the presently disclosed subject matter provides a method for treating inferior vena cava thrombosis, the method comprising: providing a presently disclosed shunt; forming one or more additional openings in the adjustable shunt region thereof, wherein the one or more additional openings are configured for delivering one or more thrombolytic agents to the inferior vena cava; optionally positioning the first balloon and the second balloon such that an area of the inferior vena cava having or suspecting of having a clot is positioned between the first and the second balloon; and implanting the shunt comprising one or more thrombolytic agents into the inferior vena cava.

Certain aspects of the presently disclosed subject matter having been stated hereinabove, which are addressed in whole or in part by the presently disclosed subject matter, other aspects will become evident as the description proceeds when taken in connection with the accompanying Figures as best described herein below.

BRIEF DESCRIPTION OF THE FIGURES

Having thus described the presently disclosed subject matter in general terms, reference will now be made to the accompanying Figures, which are not necessarily drawn to scale, and wherein:

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Adjustable, Double-Balloon Inferior Vena Cava (IVC) Shunt

The presently disclosed subject matter provides an adjustable, double-balloon IVC shunt for use in controlling blood loss and simultaneously maintaining venous return (i.e., the rate of blood flow back to the heart) in the management of IVC trauma. The double-balloon shunt provides for occlusion on both sides (proximal and distal) of an IVC injury and allows for ready access to the injury for repair. Each balloon in the shunt is independently inflatable. The double-balloon shunt is readily adjustable to fit the dimensions of the injured region.

The presently disclosed adjustable, double-balloon IVC shunt comprises two concentric, balloon-tipped catheters, which are inserted through the femoral vein (in the groin) and guided up into the IVC. After the shunt has been placed in the IVC, the two balloons are inflated by injecting saline solution using a syringe through a lumen in the wall of the tube that leads to the cavity of the balloons, thereby occluding the injured region and preventing major blood loss. The segment of the tube or shaft between the two balloons acts as a shunt, in which blood enters the shaft through slits located before the proximal balloon and then exits through similar slits after it has passed the distal balloon. Since the two balloons are on separate tubes or shafts, the distance between them can be adjusted by sliding them together or apart. This adjustability ensures that the shunt completely occludes the vein regardless of the dimensions of the patient's IVC.

Figure 1:
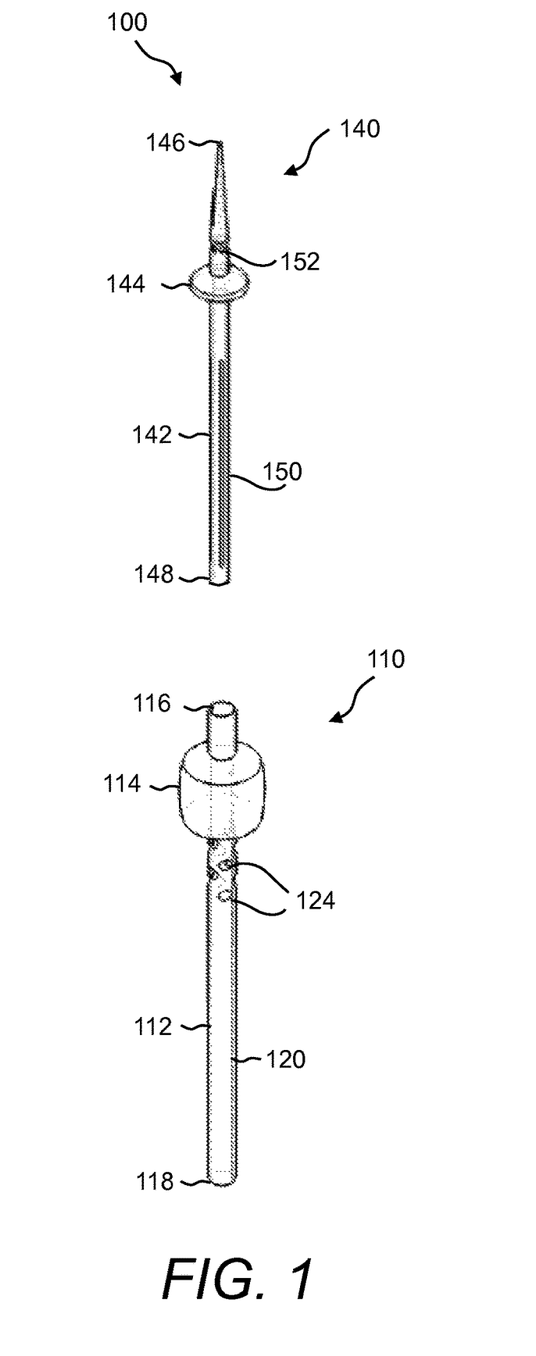
FIG. 1 illustrates a perspective view of the presently disclosed shunt comprising a first catheter unit and a second catheter unit, wherein the first catheter unit and the second catheter unit are in a separated, uncoupled state.
Figure 2:
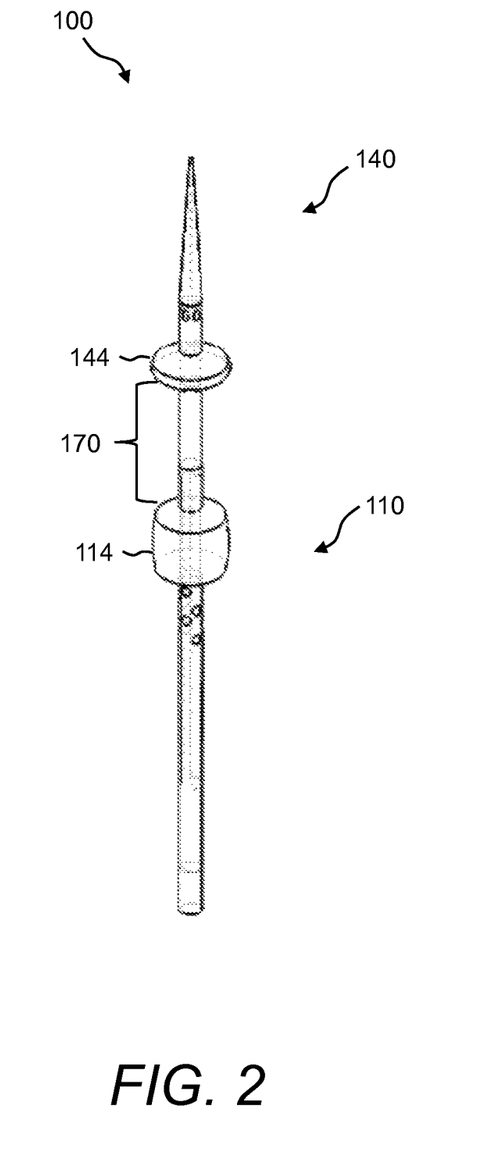
FIG. 2 illustrates a perspective view of the presently disclosed shunt, wherein the first catheter unit and the second catheter unit are slidably coupled to one another to form an adjustable shunt.

Referring now to FIG. 1, is a perspective view of the presently disclosed shunt 100 comprising a first catheter unit 110 and a second catheter unit 140, wherein the first catheter unit 110 and the second catheter unit 140 are in a separated, uncoupled state. By contrast, FIG. 2 shows the first catheter unit 110 and the second catheter unit 140 of the shunt 100 coupled together. Namely, the first catheter unit 110 and the second catheter unit 140 are formed using two concentric hollow shafts or tubes that can be slidably coupled to one another to form an adjustable shunt region 170 (see FIG. 2).

Shunt 100 can be fabricated from any material suitable for use in shunts or stents including, but not limited to, stainless steel, gold, titanium, cobalt-chromium alloy, tantalum alloy, nitinol (55% nickel and 45% titanium), niobium, platinum/iridium, and a biocompatible polymer, including, but not limited to, silicones, polyethylenes, and polyurethanes. Shunt 100 also, in some embodiments, can be coated with a biocompatible polymer, as is known in the art.

Figure 3:
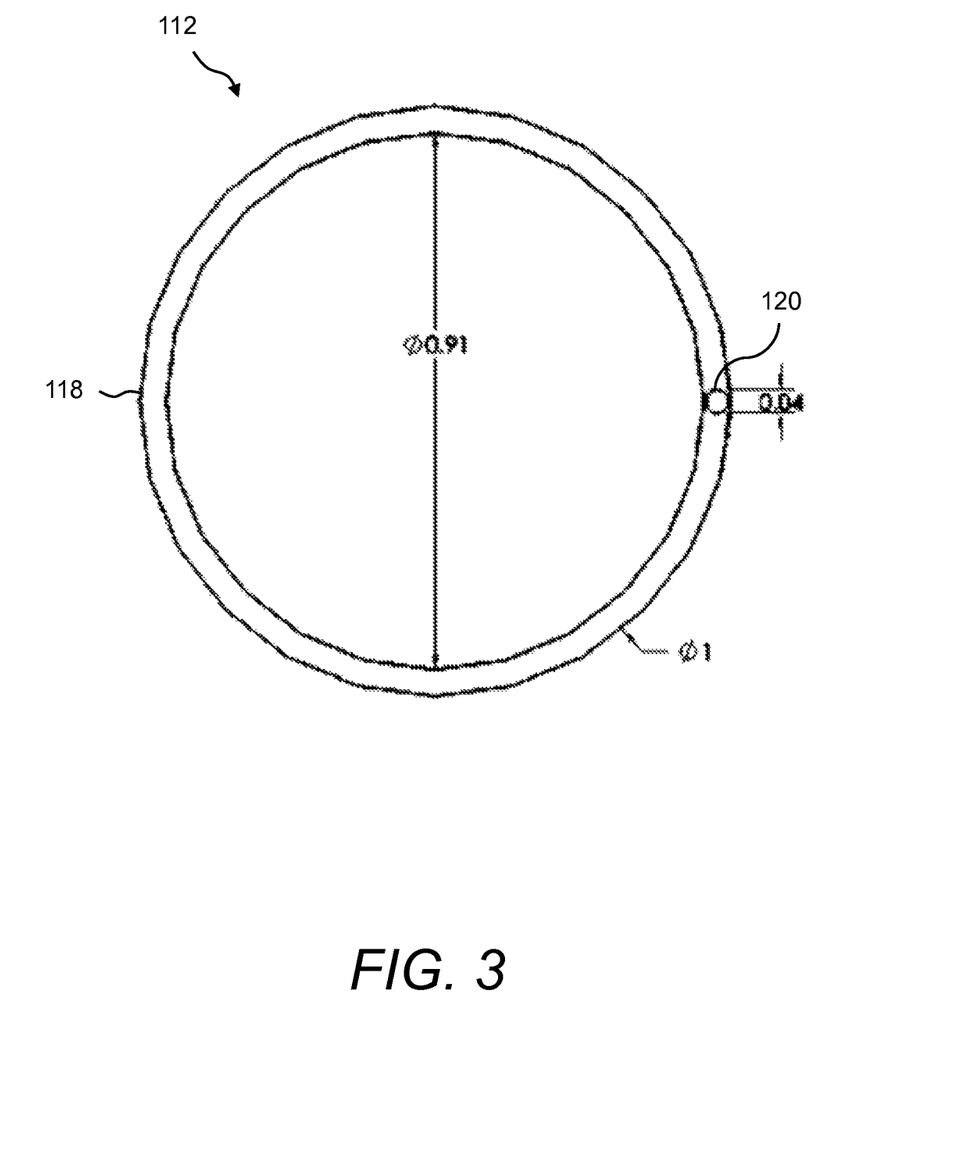
FIG. 3 illustrates an end view of a shaft of the first catheter unit shown in FIG. 1, showing example dimensions of the shaft and a lumen.
Figure 4:
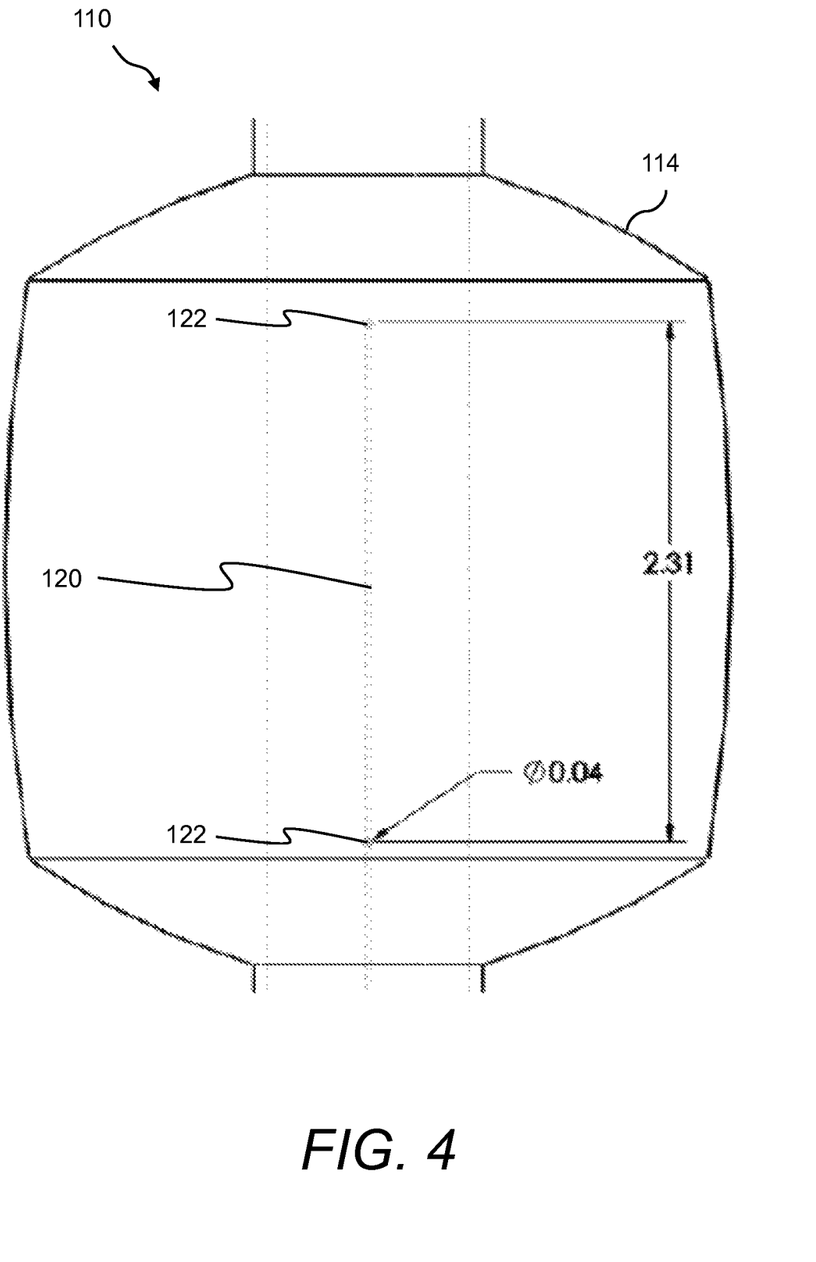
FIG. 4 illustrates a side view of a portion of the first catheter unit shown in FIG. 1, showing more details of the lumen thereof.
Figure 5:
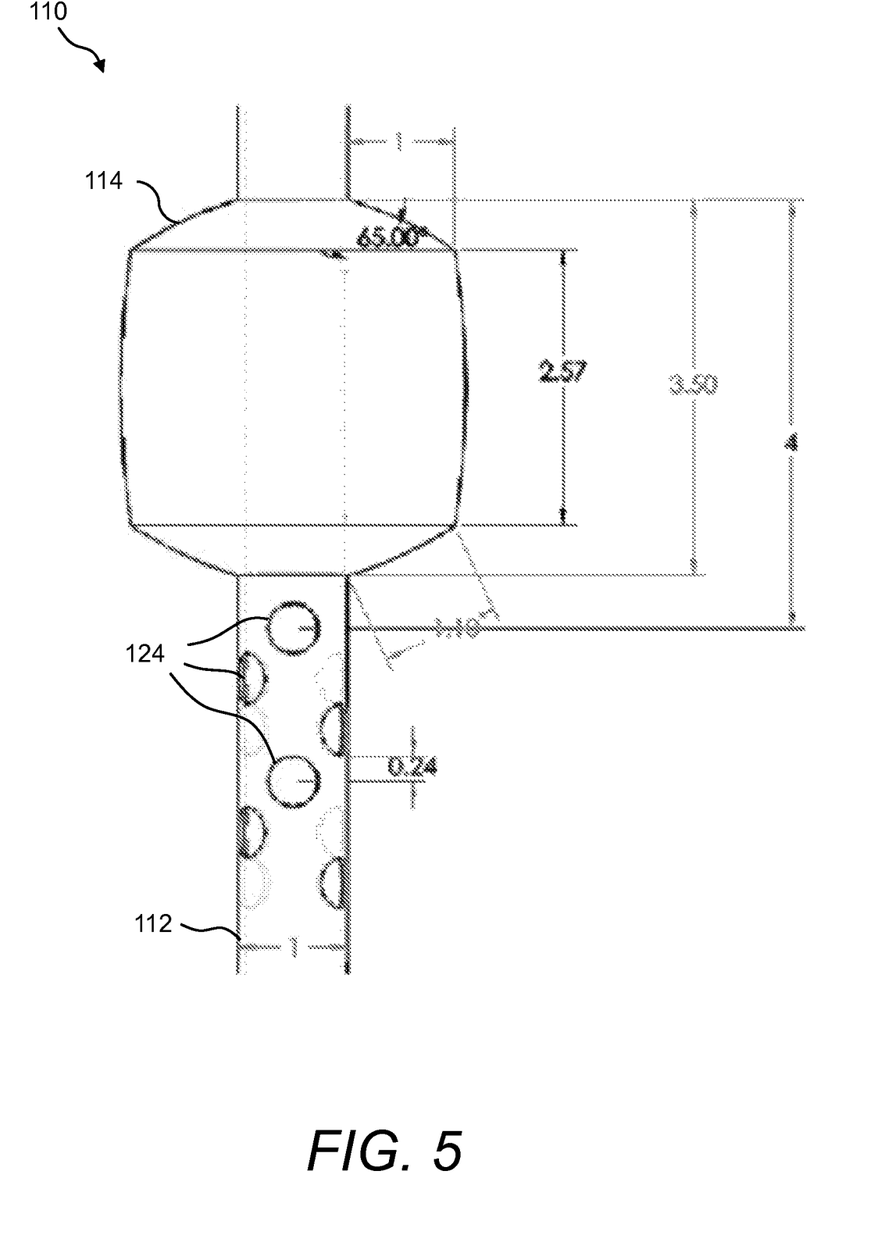
FIG. 5 illustrates a side view of a portion of the first catheter unit shown in FIG. 1, showing more details of the balloon thereof.

In addition to FIG. 1 and FIG. 2, more details of the first catheter unit 110 are shown and described below with reference to FIG. 3, FIG. 4, and FIG. 5. In addition to FIG. 1 and FIG. 2, more details of the second catheter unit 140 are shown and described below with reference to FIG. 6 through FIG. 12. Any dimensions and other specifications shown in FIG. 1 through FIG. 12 are exemplary only. The presently disclosed shunt 100 is not limited to the dimensions and other specifications shown in FIG. 1 through FIG. 12.

The first catheter unit 110 includes a shaft 112 and a balloon 114. Shaft 112 is a hollow shaft that is open at a leading end 116 and at its opposite trailing end 118. The hollow shaft 112 passes through the balloon 114, wherein the balloon 114 is sealed around the outside surface of the shaft 112. The balloon 114 is an inflatable balloon.

A lumen 120 is formed in the wall of the shaft 112 that runs along the length of the shaft 112. The lumen 120 is a channel that provides a fluid path that is used for inflating and/or deflating the balloon 114. For example and referring now to FIG. 3, an opening or inlet of the lumen 120 is provided in the trailing end 118 of the shaft 112. Outlets are provided at the opposite end of the lumen 120. Namely, the outlets of the lumen 120 are two openings 122 in the wall of the shaft 112 that are located within the cavity of the balloon 114, as shown in FIG. 4.

FIG. 3 shows an example of the dimensions of the shaft 112 of the first catheter unit 110. In this example, the shaft 112 has an outside diameter of about 1 mm and an inside diameter of about 0.91 mm. Therefore, the thickness of the wall of the shaft 112 is about 0.09 mm. FIG. 3 also shows that the diameter of the lumen 120 is about 0.04 mm. FIG. 4 shows that each of the openings 122 also has a diameter of about 0.04 mm. The two openings 122 are spaced, for example, about 2.31 mm apart. Liquid (e.g., saline) or air can be flowed through the lumen 120 and out of the openings 122 and into balloon 114 to inflate the balloon 114 during use. In one example, a syringe (not shown) is used to inject saline into the lumen 120. Additionally, liquid (e.g., saline) or air can be flowed out of the balloon 114 through the openings 122 and into the lumen 120 to deflate the balloon 114. In one example, a syringe (not shown) is used to pull saline out of the balloon 114, through openings 122 and the lumen 120.

A plurality of openings 124 (e.g., ten openings 124) are provided in the shaft 112 near the balloon 114, as shown in FIG. 5. The openings 124 provide a fluid path for venous blood into the shaft 112 of the first catheter unit 110. FIG. 5 also shows that the ends of the balloon 114 are slightly curved or tapered to reduce eddy current as fluid is flowed into shunt 100. Example dimensions of the balloon 114 are also shown in FIG. 5. The openings 122 are formed in a spiraling pattern in the shaft 112 and have a lateral spacing along the length of the shaft 112 of about 0.24 mm edge-to-center. Because the openings 122 are arranged in a spiraling pattern, the rate at which fluid (i.e., blood) flows into the shaft 112 via the openings 122 is optimized.

The second catheter unit 140 includes a shaft 142 and a balloon 144. The hollow shaft 142 passes through the balloon 144, wherein the balloon 144 is sealed around the outside surface of the shaft 142. Balloon 144 is an inflatable balloon. The shaft 142 is a hollow shaft that has a leading end 146 and a trailing end 148. The leading end 146 of the shaft 142 tapers to a point and is closed, while the opposite trailing end 148 is open. For the shaft 142 of second catheter unit 140 to be slidably fitted into the shaft 112 of first catheter unit 110, the outside diameter of the shaft 142 must be smaller than the inside diameter of the shaft 112 of the first catheter unit 110.

Figure 6:
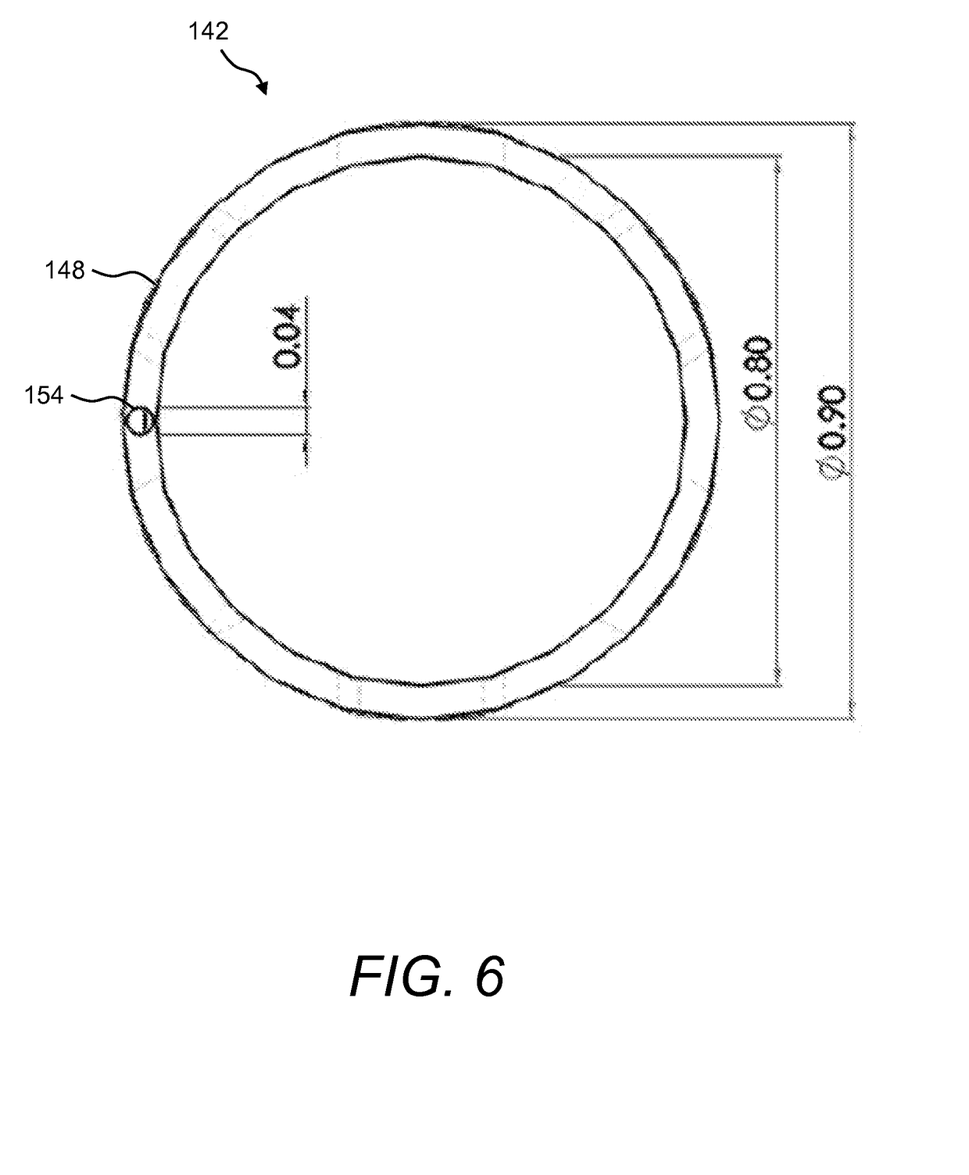
FIG. 6 illustrates an end view of a shaft of the second catheter unit shown in FIG. 1, showing example dimensions of the shaft and a lumen.
Figure 7:
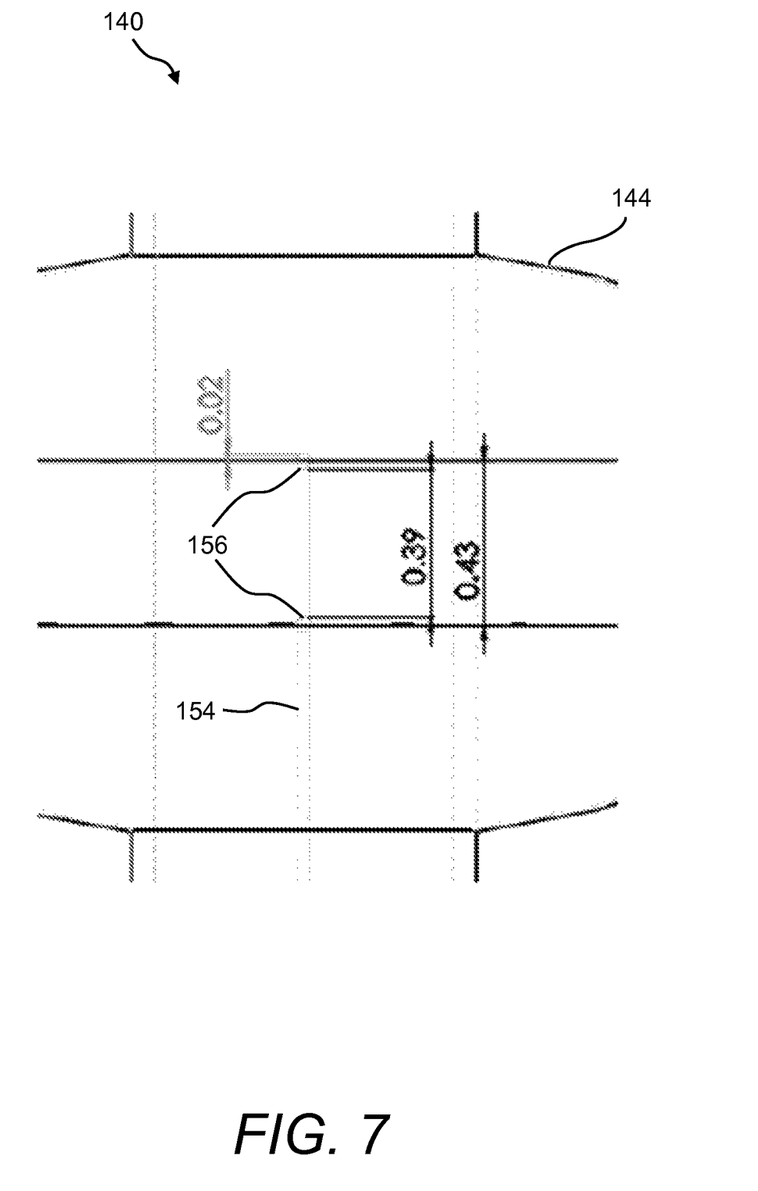
FIG. 7 illustrates a side view of a portion of the second catheter unit shown in FIG. 1, showing the position of the lumen and openings relative to the balloon.
Figure 8:
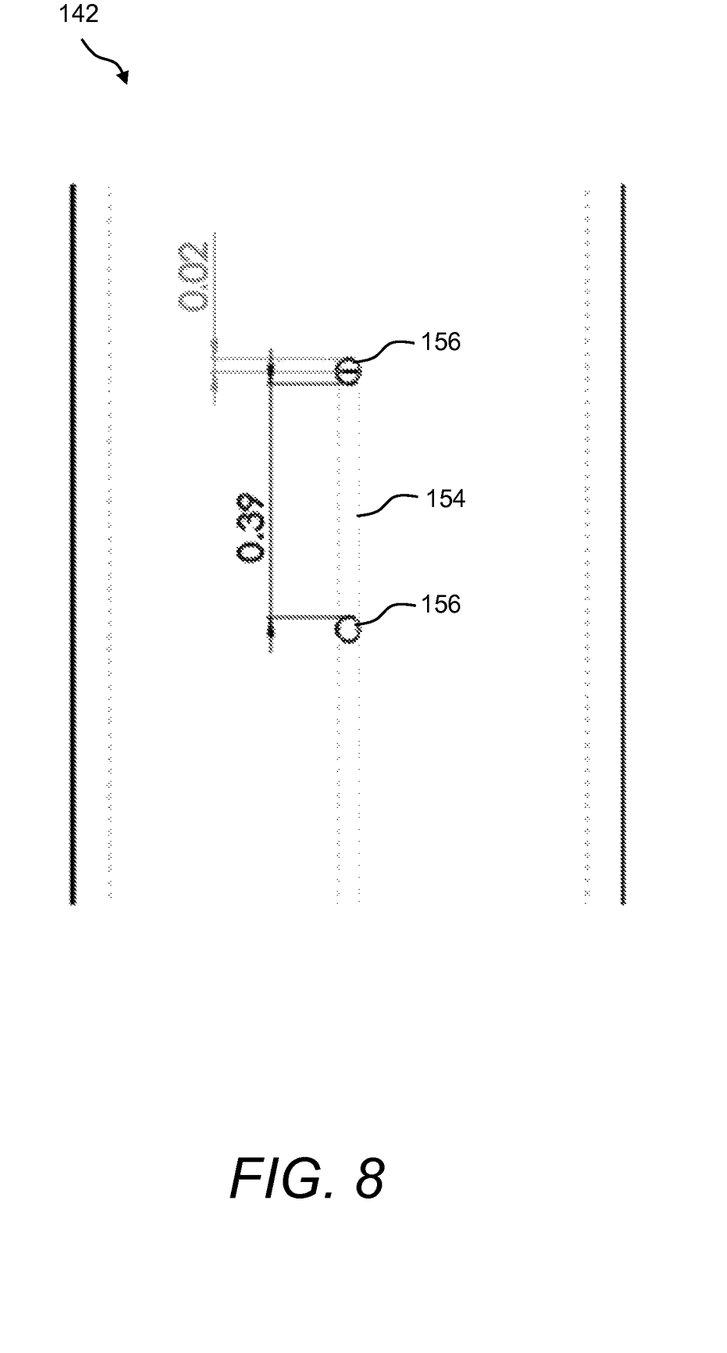
FIG. 8 illustrates a side view of a portion of the second catheter unit shown in FIG. 1, showing more details of the lumen.

FIG. 6 shows an example of the cross-sectional dimensions of the shaft 142 of the second catheter unit 140. In this example, the shaft 142 has an outside diameter of about 0.9 mm and an inside diameter of about 0.8 mm. Therefore, the thickness of the wall of the shaft 142 is about 0.1 mm. Also shown in FIG. 6 is a lumen 154 that is formed in the wall of the shaft 142 that runs along the length of shaft 142. The lumen 154 is a channel that provides a fluid path that is used for inflating and/or deflating the balloon 144. For example, FIG. 6 shows that an opening or inlet of the lumen 154 is provided in the trailing end 148 of the shaft 142. In one example, the diameter of lumen 154 is about 0.04 mm. Outlets are provided at the opposite end of the lumen 154. Namely, the outlets of the lumen 154 are two openings 156 in the wall of shaft 142 that are located within the cavity of the balloon 144, as shown in FIG. 7 and FIG. 8. Namely, FIG. 7 shows the two openings 156 with respect to the balloon 144 and FIG. 8 shows a close up view of the two openings 156 and the lumen 154.

FIG. 7 and FIG. 8 show that each of the openings 156 has a diameter of about 0.04 mm. Further, in one example, the on-center spacing of the two openings 156 is about 0.41 mm. Liquid (e.g., saline) or a gas, such as air or nitrogen, can be flowed through lumen 154 and out of openings 156 and into the balloon 144 to inflate the balloon 144 during use. In one example, a syringe (not shown) is used to inject saline into the lumen 154. Additionally, liquid (e.g., saline) or a gas, such as air or nitrogen, can be flowed out of the balloon 144 through (not shown) is used to pull saline out of the balloon 144, through openings 156 and the lumen 154. It should be noted that the balloon 144 of the second catheter unit 140 and the balloon 114 of the first catheter unit 110 can be inflated and deflated independently.

Figure 9:
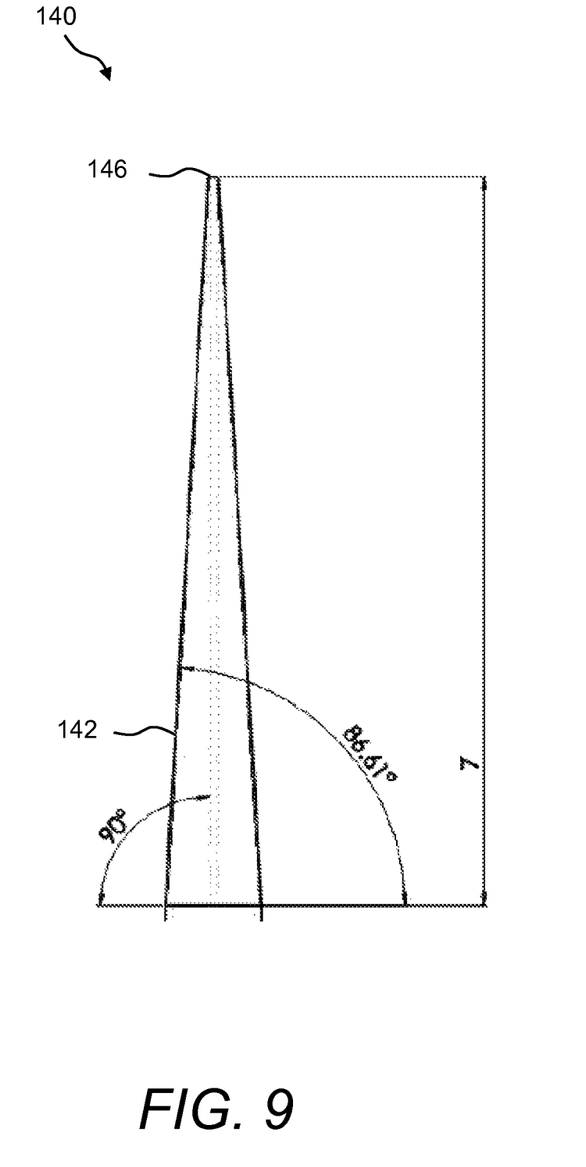
FIG. 9 illustrates a side view of a portion of the second catheter unit shown in FIG. 1, showing the tapered end thereof.

More details of an example of the leading end 146 of the shaft 142 are shown in FIG. 9. In the example shown in FIG. 9, the tapered or cone-shaped leading end 146 of the shaft 142 is about 7 mm long and is tapered at an angle of about 86.61 degrees per the indications shown in FIG. 9.

Figure 10:
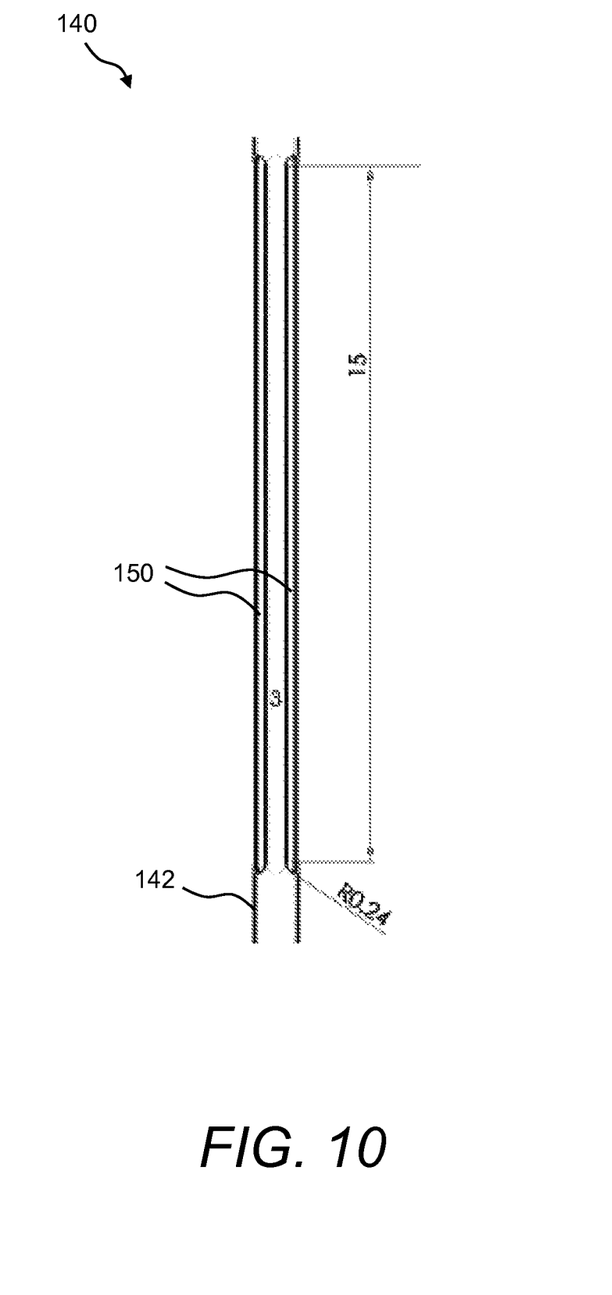
FIG. 10 illustrates a perspective view of a portion of the shaft of the second catheter unit shown in FIG. 1, showing more details of the slits thereof.

Referring again to FIG. 1, FIG. 1 also shows that a plurality of slits 150 (i.e., three slits 150) are formed in the shaft 142 of the second catheter unit 140. For example, three slits 150 are provided along the length of the shaft 142, between the balloon 144 and the trailing end 148 of the shaft 142. The slits 150 provide a fluid path for venous blood into the shaft 142 of the second catheter unit 140. Referring now to FIG. 10, which shows more details of the slits 150 in the shaft 142, in one example, each of the slits 150 is about 15 mm in length. Further, the three slits 150 are spaced about 120 degrees apart around the circumference of the shaft 142.

Figure 11:
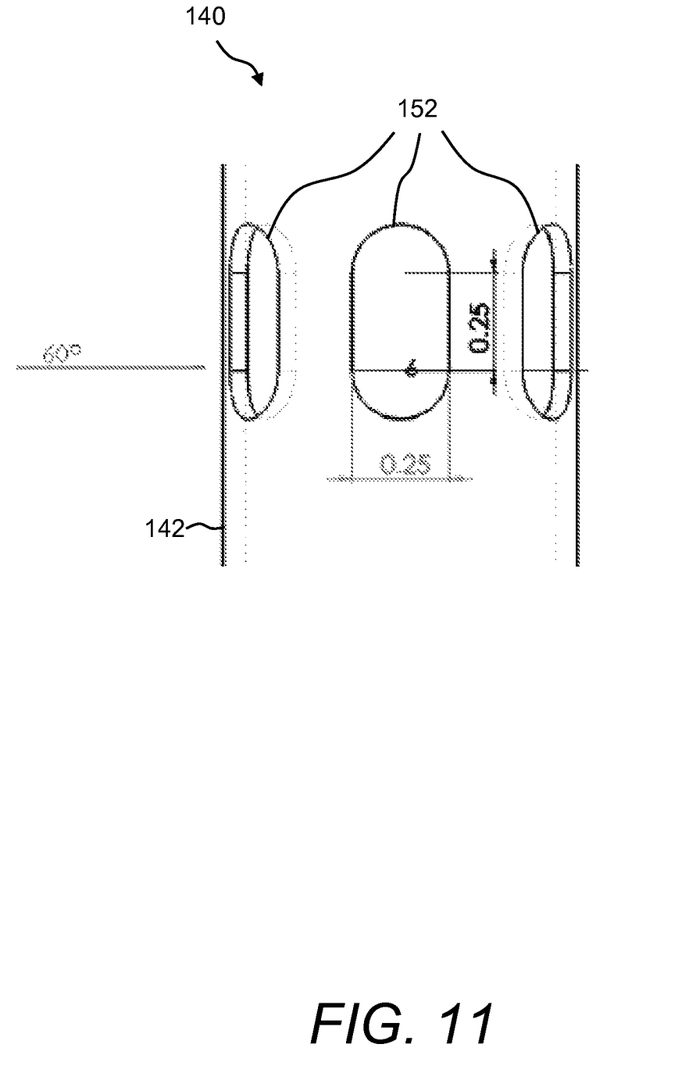
FIG. 11 illustrates a perspective view of another portion of the shaft of the second catheter unit shown in FIG. 1, showing more details of the openings thereof.

Referring again to FIG. 1, a plurality of openings 152 (i.e., six openings 152) are provided in the shaft 142 of the second catheter unit 140. The openings 152 provide a fluid path for venous blood out of the shaft 142 of the second catheter unit 140. Referring now to FIG. 11, which shows more details of the openings 152 in the shaft 142, in one example, the six openings 152 are spaced about 60 degrees apart around the circumference of the shaft 142. Each of openings 152 is, for example, oblong, not circular. For example, each of the openings 152 is about 0.25 mm wide and about 0.5 mm high.

Figure 12:
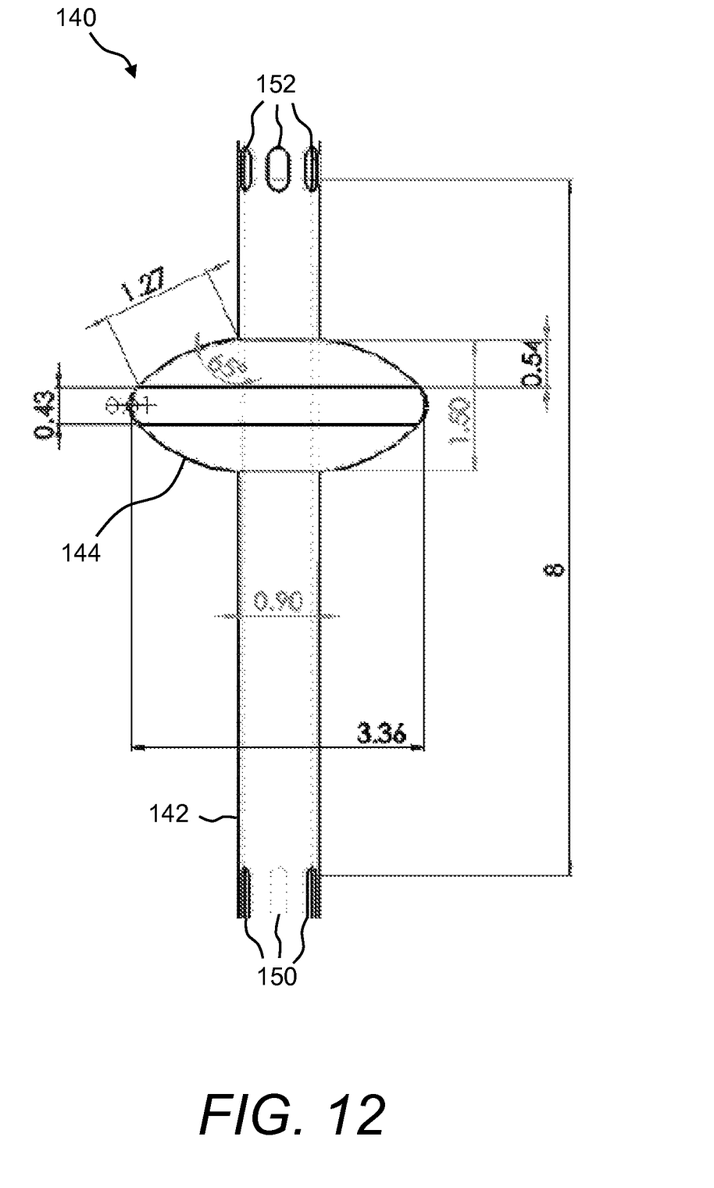
FIG. 12 illustrates a side view of a portion of the second catheter unit shown in FIG. 1, showing more details of the shaft and the balloon.

Referring now to FIG. 12, the balloon 114 is positioned along the shaft 142, between the slits 150 and the openings 152. The top (i.e., toward openings 152) and bottom (i.e., toward slits 150) of the balloon 144 are slightly curved or tapered to reduce eddy current. FIG. 12 also shows that the spacing between the top of the slits 150 and the bottom of the openings 152 is about 8 mm.

The first catheter unit 110 and the second catheter unit 140 are concentric catheters, wherein the trailing end 148 of the shaft 142 of the second catheter unit 140 is inserted into the leading end 116 of the shaft 112 of the first catheter unit 110 in slidable fashion. Because the second catheter unit 140 can slide within the first catheter unit 110, the distance between the balloon 144 of the second catheter unit 140 and the balloon 114 of the first catheter unit 110 may be readily adjusted to fit the dimensions of the injured region. That is, the size of the shunt region 170 (see FIG. 2) may be readily adjusted to fit the dimensions of the injured region.

Figure 13:
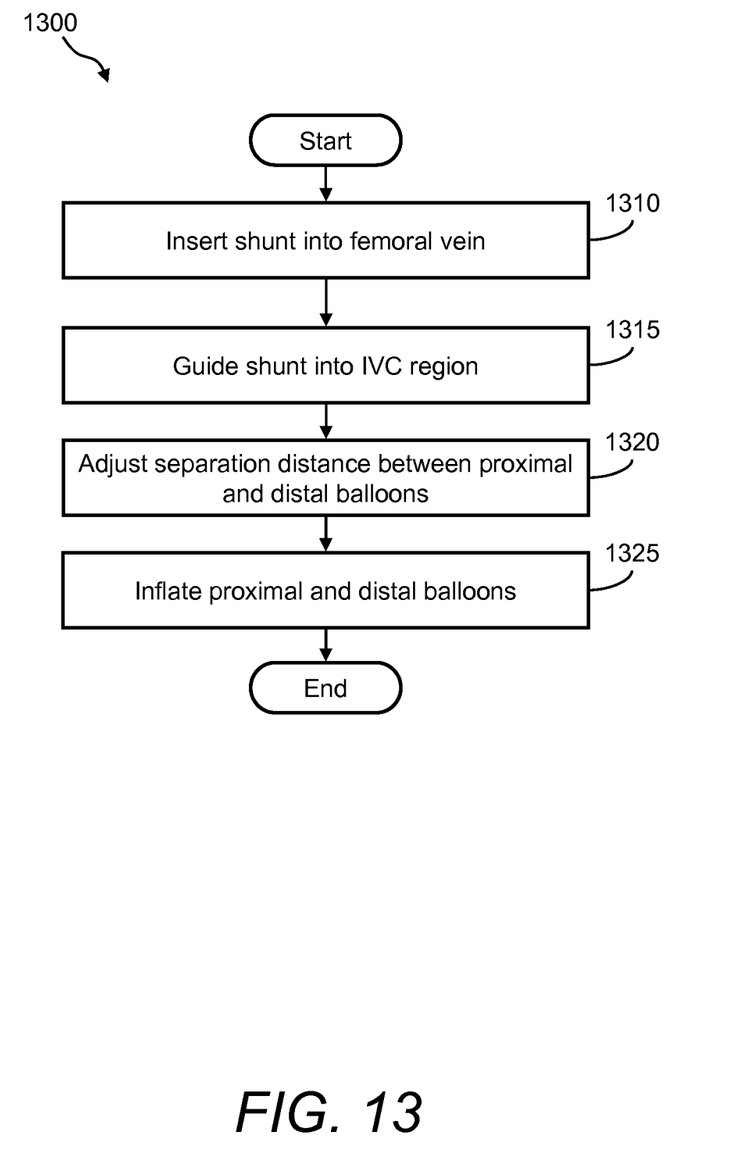
FIG. 13 illustrates a flow diagram of a method of inserting and inflating the shunt for occluding an injured region and controlling blood loss.

FIG. 13 illustrates a flow diagram of an example of a method 1300 of using the presently disclosed shunt 100 to occlude an injured area and control blood loss while simultaneously maintaining venous return. Method 1300 uses the slidably coupled shunt 100 shown in FIG. 2. Method 1300 includes, but is not limited to, the following steps.

At a step 1310, the shunt 100 is inserted into the femoral vein (in the groin) of the patient or subject of the procedure.

At a step 1315, the shunt 100 is guided up into the inferior vena cava to the site of injury.

At a step 1320, the distance between the balloon 114 of the first catheter unit 110 and the balloon 144 of the second catheter unit 140 is adjusted to fit the dimensions of the injured region. The distance between the balloon 114 of the first catheter unit 110 and the balloon 144 of the second catheter unit 140 adjusted by sliding the second catheter unit 140 further into or out of the first catheter unit 110. The adjustability of the presently disclosed shunt 100 ensures that shunt 100 occludes the injured region of the vein regardless of the dimensions of the subject's or patient's inferior vena cava.

At a step 1325, the balloon 114 of the first catheter unit 110 and the balloon 144 of the second catheter unit 140 are independently inflated. The balloon 114 of the first catheter unit 110 is inflated using, for example, saline. In one example, a syringe is used to inject saline into lumen 120. The saline solution flows out of lumen 120 via openings 122 and into the cavity of the balloon 114, thereby inflating the balloon 114 of the first catheter unit 110. The inflated balloon 114 occludes the proximal side of an injured region (i.e., toward lower portion of the IVC). The balloon 144 of the second catheter unit 140 is inflated using, for example, saline. In one example, a syringe is used to inject saline into the lumen 154. The saline solution flows out of lumen 154 via openings 156 and into the cavity of the balloon 144, thereby inflating the balloon 144. The inflated balloon 144 occludes the distal side of an injured region (i.e., toward the heart). The shunt region 170 (see FIG. 2) maintains blood flow during repair of the injured region; namely, blood enters the first catheter unit 110 via the openings 124, flows through shunt region 170, and exits the second catheter unit 140 via the openings 152.

In another embodiment, the presently disclosed shunt 100 may be modified for use in the delivery of chemotherapeutic drugs for the treatment of primary and metastatic liver cancer. For example, additional openings may be formed in the region between balloon 114 and balloon 144 (i.e., shunt region 170) for delivery of the chemotherapeutic drugs to the liver.

In another embodiment, shunt 100 may be modified for use in the treatment of IVC thrombosis. For example, additional openings may be formed in the region between the balloon 114 of the first catheter unit 110 and the balloon 144 of the second catheter unit 140 (i.e., shunt region 170) for delivery of thrombolytic agents. The balloon 114 of the first catheter unit 110 and the balloon 144 of the second catheter unit 140 may be positioned such that the clot is located between the balloons.

The subject treated by the presently disclosed methods in their many embodiments is desirably a human subject, although it is to be understood that the methods described herein are effective with respect to all vertebrate species, which are intended to be included in the term "subject."

A "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. An inferior vena cava shunt comprising:
   a first catheter and a second catheter, wherein the first catheter and the second catheter are formed from two concentric hollow shafts that can be slidably coupled to one another to form an adjustable shunt region;
   wherein the first catheter comprises a first hollow shaft and a first inflatable balloon, wherein the first inflatable balloon is sealed around an outside surface of the first hollow shaft, and wherein the first hollow shaft is open at a leading end and open at an opposite trailing end, and wherein the first hollow shaft passes through the first inflatable balloon;

wherein the first catheter further comprises a lumen formed in a wall of the first hollow shaft, wherein the lumen comprises one or more channels configured to provide a fluid path for inflating and/or deflating the first inflatable balloon, wherein the lumen comprises one or more inlets at an end of the lumen proximate to the trailing end of the first hollow shaft and one or more outlets at an opposite end of the lumen, and wherein the one or more outlets is located within a cavity of the first inflatable balloon;

wherein the first hollow shaft further comprises a plurality of openings configured to provide a fluid path for venous blood into the first hollow shaft; and wherein the second catheter comprises a second hollow shaft and a second inflatable balloon, wherein the second inflatable balloon is sealed around an outside surface of the second hollow shaft, and wherein the second hollow shaft is tapered and closed at a leading end and open at an opposite trailing end, and wherein the second hollow shaft passes through the second inflatable balloon;

wherein an outside diameter of the second hollow shaft is smaller than an inside diameter of the first hollow shaft such that the second hollow shaft can be slidably fitted into the first hollow shaft;

wherein the second catheter further comprises a lumen formed in a wall of the second hollow shaft, wherein the lumen comprises one or more channels configured to provide a fluid path for inflating and/or deflating the second inflatable balloon, wherein the lumen comprises one or more inlets at an end of the lumen proximate to the trailing end of the second hollow shaft and one or more outlets at an opposite end of the lumen, and wherein the one or more outlets is located within a cavity of the second inflatable balloon;

wherein the second hollow shaft further comprises a plurality of slits running longitudinally along the length of the second hollow shaft from the trailing end of the second hollow shaft to the opposite end thereof; and wherein the second hollow shaft further comprises a plurality of openings configured to provide a fluid path for venous blood out of the second hollow shaft; and wherein the first inflatable balloon and the second inflatable balloon can be inflated or deflated independently.

2. The inferior vena cava shunt of claim 1, wherein the openings of the first hollow shaft comprise a spiral pattern.

3. The inferior vena cava shunt of claim 1, wherein a length of the inferior vena cava shunt can be varied to fit an injured region of an inferior vena cava by adjusting the adjustable shunt region.

4. A method for occluding an injured area of an inferior vena cava while maintaining venous return thereto, the method comprising:
providing an inferior vena cava shunt of claim 1;
inserting the shunt into a femoral vein of a subject;
guiding the shunt into the inferior vena cava to the injured area;
adjusting a distance between the first inflatable balloon of the first catheter and the second balloon of the second catheter to fit one or more dimensions of the injured region, wherein the distance is adjusted by sliding the second catheter into or out of the first catheter;
inflating the first inflatable balloon and the second inflatable balloon, wherein the inflated first balloon occludes a proximal side of the injured area and the inflated second balloon occludes the distal side of the injured area; and
wherein the adjustable shunt region maintains blood flow to the injured area.

5. A method for delivering a chemotherapeutic agent for treating a liver cancer, the method comprising:
providing a shunt of claim 1;
forming one or more additional openings in the adjustable shunt region thereof, wherein the one or more additional openings are configured for delivering one or more chemotherapeutic agents to the liver; and
implanting the shunt comprising one or more chemotherapeutic agents into the inferior vena cava for delivering the one or more chemotherapeutic agents to the liver.

6. A method for treating inferior vena cava thrombosis, the method comprising:
providing a shunt of claim 1;
forming one or more additional openings in the adjustable shunt region thereof, wherein the one or more additional openings are configured for delivering one or more thrombolytic agents to the inferior vena cava;
optionally positioning the first balloon and the second balloon such that an area of the inferior vena cava having or suspecting of having a clot is positioned between the first and the second balloon; and
implanting the shunt comprising one or more thrombolytic agents into the inferior vena cava.

* * * * *